United States Patent [19]

Foulletier et al.

[11] 3,997,604

[45] Dec. 14, 1976

[54] MIXTURES OF PERFLUOROALIPHATIC SUBSTITUTED AMINO COMPOUNDS AND THE METHOD FOR PREPARING THE SAME

[75] Inventors: Louis Foulletier, Ouillins; Jean-Pierre Lalu, La Mulatieres, both of France

[73] Assignee: Produits Chimiques Ugine Kuhlmann, France

[22] Filed: Apr. 29, 1971

[21] Appl. No.: 138,810

Related U.S. Application Data

[63] Continuation-in-part of Ser. Nos. 694,081, Dec. 28, 1967, abandoned, and Ser. No. 819,480, April 25, 1969, abandoned.

[30] Foreign Application Priority Data

Jan. 2, 1967 France .............................. 67.89676
Sept. 15, 1967 France .......................... 67.121188
Nov. 7, 1967 France ............................ 67.127254
Apr. 29, 1968 France .......................... 68.149848

[52] U.S. Cl. .............................. 260/561 N; 8/115.6
[51] Int. Cl.² ........................................ C07C 103/58
[58] Field of Search ................................ 260/561 N

[56] References Cited

UNITED STATES PATENTS

| | | | |
|---|---|---|---|
| 2,521,902 | 9/1950 | Coover, Jr. et al. | 260/561 N X |
| 2,782,184 | 2/1957 | Husted et al. | 260/561 N X |
| 2,957,914 | 10/1960 | Halpern et al. | 260/561 N |
| 3,535,381 | 10/1970 | Hauptschein et al. | 260/561 N X |

*Primary Examiner*—Ethel G. Love
*Attorney, Agent, or Firm*—Pennie & Edmonds

[57] ABSTRACT

This invention comprises perfluoroaliphatic substituted amino compounds of the formula

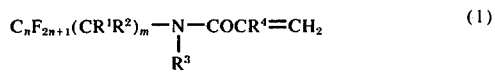 (1)

wherein $n$ is an integer from 6 to 20, $m$ is 2 or 4, $R^1$ and $R^2$ each is hydrogen atom or a lower alkyl with 1 to 3 carbon atoms, $R^3$ is a hydrogen atom, an alkyl containing 1 to 29 carbon atoms, an alkenyl containing 3 to 10 carbon atoms, a cycloalkyl radical containing 3 to 12 carbon atoms, a cycloalkenyl with 5 to 12 carbon atoms, an N or O ring substituted cycloalkenyl radical containing 5 to 12 carbon atoms, an aryl, the radical —$(CHR)_1$—OH wherein R is a hydrogen atom or a lower alkyl containing 1 to 3 carbon atoms, and $R^4$ is a hydrogen atom or a methyl group and the method for preparing the same. This invention also comprises perfluoroaliphatic substituted amino compounds of the formula

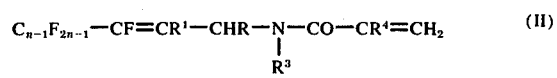 (II)

and mixtures of products of formula II with compounds of the formula

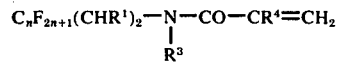

and the method for preparing the same. The compounds are strong oleophobic and hydrophobic agents.

9 Claims, No Drawings

MIXTURES OF PERFLUOROALIPHATIC SUBSTITUTED AMINO COMPOUNDS AND THE METHOD FOR PREPARING THE SAME

CROSS REFERENCE TO RELATED APPLICATIONS

This application is a continuation-in-part of our prior application Ser. No. 694,081, filed Dec. 28, 1967, now abandoned, and our application Ser. No. 819,480 filed Apr. 25, 1969, now abandoned.

FIELD OF THE INVENTION

This invention relates to perfluoroaliphatic substituted amino compounds containing acrylic groups and the method for preparing the same.

DESCRIPTION OF THE PRIOR ART

It is well known that nonfluorinated alkyl halides of the formula $$C_nH_{2n+1}X$$

wherein $n$ is an integer and X is a halogen, react with ammonia and with amines to produce various substituted amine and quaternary ammonium salts. However, in the case of fluorinated alkyl halides of the formula $$C_nF_{2n+1}-CH_2CH_2-X$$

wherein $n$ and X each has the same meaning as stated above, the halides become readily dehydrohalogenated in the presence of nucleophilic agents such as various amines which include the tertiary amine to yield fluorinated olefins of the formula $$C_nF_{2n+1}-CH=CH_2$$

SUMMARY OF THE INVENTION

We have discovered that it is possible according to the method of this invention to prepare a perfluoroalkyl substituted amino compound of the formula $$C_nF_{2n+1}(CR^1R^2)_m-N-CO-CR^4=CH_2 \quad (I)$$
$$\phantom{C_nF_{2n+1}(CR^1R^2)_m-N}|$$
$$\phantom{C_nF_{2n+1}(CR^1R^2)_m-N}R^3$$

wherein $n$ is an integer from 6 to 20, $m$ is 2 or 4, $R^1$ and $R^2$ each is hydrogen atom or a lower alkyl with 1 to 3 carbon atoms, $R^3$ is a hydrogen atom, an alkyl containing 1 to 20 carbon atoms, an alkenyl containing 3 to 10 carbon atoms, a cycloalkyl radical containing 3 to 12 carbon atoms, a cycloalkenyl with 5 to 12 carbon atoms, and N or O ring substituted cycloalkenyl radical containing 5 to 12 carbon atoms, an aryl, the radical of $-(CHR)_q-OH$ wherein R is a hydrogen atom or a lower alkyl containing 1 to 3 carbon atoms, and $R^4$ is a hydrogen atom or a methyl group, by reacting at a temperature between 0° and 200° C. and in the presence of a polymerization inhibitor and with or without a transesterification catalyst, a hydracid acceptor or a water acceptor, a. a perfluoroalkyl amine of the formula $$C_nF_{2n+1}(CR^1R^2)_mN-R^3 \quad (IV)$$
$$\phantom{C_nF_{2n+1}(CR^1R^2)_mN}|$$
$$\phantom{C_nF_{2n+1}(CR^1R^2)_mN}H$$

wherein $n$, $m$, $R^1$, $R^2$ and $R^3$ have the same meaning as stated above with b. an acrylic compound of the formula $$XCOCR^4=CH_2 \quad V.$$

wherein X is $-Cl$, $-OH$, $-O-COCR^4=CH_2$ or an alkoxy radical with 1 to 8 carbon atoms and $R^4$ has the same meaning as stated above. Perfluoroaliphatic amines of the formula $$C_nF_{2n+1}(CHR^1)_2N-R^3 \quad (VI)$$
$$\phantom{C_nF_{2n+1}(CHR^1)_2N}|$$
$$\phantom{C_nF_{2n+1}(CHR^1)_2N}H$$

together with perfluoroaliphatic amines of the formula $$C_{n-1}F_{2n-1}-CF=CR^1-CHR^1-N-R^3 \quad (VII)$$
$$\phantom{C_{n-1}F_{2n-1}-CF=CR^1-CHR^1-N}|$$
$$\phantom{C_{n-1}F_{2n-1}-CF=CR^1-CHR^1-N}H$$

wherein $R^1$ and $R^3$ have the same meaning as stated above and $n$ is an integer from 4 to 20 when reacted with an acrylic compound corresponding to formula V according to the process of this invention, simultaneously yield compounds having the formula $$C_nF_{2n+1}(CHR^1)_2-N-COCR^4=CH_2 \quad (III)$$
$$\phantom{C_nF_{2n+1}(CHR^1)_2-N}|$$
$$\phantom{C_nF_{2n+1}(CHR^1)_2-N}R^3$$

together with compounds of the formula $$C_{n-1}F_{2n-1}-CF=CR^1-CHR^1-N-COCR^4=CH_2 \quad (II)$$
$$\phantom{C_{n-1}F_{2n-1}-CF=CR^1-CHR^1-N}|$$
$$\phantom{C_{n-1}F_{2n-1}-CF=CR^1-CHR^1-N}R^3$$

wherein $R^1$, $R^3$ and $R^4$ have the same meaning as previously stated and $n$ is an integer from 4 to 20.

DESCRIPTION OF THE PREFERRED EMBODIMENT

The perfluoroaliphatic amines suitable for this invention are prepared according to our copending United States application filed concurrently herewith, entitled "Perfluoroaliphatic Substituted Amines and the Method for Preparing the Same." It is therein disclosed that perfluoroalkyl amines of the formula $$C_nF_{2n+1}(CR^1R^2)_mN-R^3 \quad (VIII)$$
$$\phantom{C_nF_{2n+1}(CR^1R^2)_mN}|$$
$$\phantom{C_nF_{2n+1}(CR^1R^2)_mN}H$$

wherein $n$, $m$, $R^1$ and $R^2$ have the same meaning as designated above and R is an alkyl containing 1 to 20 carbon atoms, an alkenyl containing 3 to 10 carbon atoms, a cycloparaffin radical containing 3 to 12 carbon atoms, a cylkoalkenyl radical containing 3 to 12 carbon atoms, an N or O ring substituted cycloakenyl radical containing 5 to 12 carbon atoms, or an aryl are prepared by reacting at a temperature in the range between 0° and 200° C. perfluoroalkyl halides of the formula $$C_nF_{2n+1}(CR^1R^2)_mY \qquad \text{IX.}$$

wherein $n$, $m$, $R^1$ and $R^2$ each has the same meaning as defined hereinabove and Y is an iodine or a bromine atom with amines of the formula $$HN\begin{smallmatrix}R^3\\ \\H\end{smallmatrix} \qquad \text{(X)}$$

wherein $R^3$ has the same meaning as stated for formula VIII. It is also disclosed therein that perfluoroaliphatic substituted amines of the formula $$C_nF_{2n+1}(CHR^1)_2-\underset{\underset{H}{|}}{N}-R^3 \qquad \text{(XI)}$$

and mixtures of XI with compounds of the formula $$C_{n-1}F_{2n-1}-CF=CR^1-CHR^1-\underset{\underset{H}{|}}{N}-R^3 \qquad \text{(XII)}$$

are prepared in the same manner as compounds of formula VIII except that in the starting compounds of formula VIII, at least one of the radicals $R^1$ or $R^2$ is hydrogen, $m$ is equal to 2 and $n$ is an integer between 4 and 20. The preferred perfluoroaliphatic amines of this invention are compounds XI together with XII.

The perfluoroaliphatic amino alcohols suitable for this invention are prepared by the method disclosed according to our copending United States application filed concurrently herewith entitled, "Perfluoroaliphatic Substituted Amino Alcohols and the Method for Preparing the Same" also filed concurrently herewith. It is therein disclosed that perfluoroaliphatic substituted amino alcohols of the formula $$C_nF_{2n+1}(CR^1R^2)_m\underset{\underset{H}{|}}{N}-(CHR)_qOH \qquad \text{(XIII)}$$

wherein $n$, $m$, $R^1$, $R^2$ and $R$ and $q$ have the same meaning as stated above are prepared by reacting at a temperature in the range between 20° and 200° C. perfluoroalkyl halides of the formula $$C_nF_{2n+1}(CR^1R^2)_mY \qquad \text{IX.}$$

with an amino alcohol of the formula $$H_2N(CHR)_qOH \qquad \text{XIV.}$$

wherein R and $q$ have the same meaning as previously stated. It is also disclosed therein that perfluoroaliphatic substituted amino alcohols of the formula $$C_nF_{2n+1}(CHR^1)_2-\underset{\underset{H}{|}}{N}-(CHR)_qOH \qquad \text{(XV)}$$

and mixtures of XV with compounds of the formula $$C_{n-1}F_{2n-1}-CF=CR^1-CHR^1-\underset{\underset{H}{|}}{N}-(CHR)_qOH \qquad \text{(XVI)}$$

are prepared in the same manner as formula XIII compounds except that in the starting compounds of formula XIII, at least one of the radicals $R^1$ or $R^2$ is hydrogen, $m$ is equal to 2 and $n$ is an integer between 4 and 20. The preferred perfluoroaliphatic amino alcohols of this invention are compounds XV together with XVI.

In the reaction where X of formula V is a atom, atome, the operation is carried out in the presence of a hydracid acceptor such as the tertiary amines, for example, trimethylamine, triethylamine, tripropylamine, tributylamine, tripentylamine and pyridine.

In the case where X is the OH group, the operation is carried out in the presence of a water captor such as sulfuric acid, or a molecular sieve. The water can also be eliminated by azeotropic distillation using a solvent which is inert with respect to the reactants.

In the case where X is an alkoxy group, the operation is carried out with or without a transesterification catalyst such as acid or basic catalysts, for example, sulfuric acid, para-toluene-sulfonic acid, and acid resin, and aluminum alcoholate. The alcohol formed in the reaction medium may be retained or it may be eliminated during the reaction.

The fluorinated compounds according to the invention have interesting and varied applications. Thus, the monomers obtained can be polymerized or copolymerized with other acrylic, methacrylic, or vinylic molecules by the usual methods.

These strongly fluorinated polymers and copolymers used in solution or in dispersion, are extremely powerful oleophobic and hydrophobic agents. Their chemical stability and especially their resistance to hydrolysis makes it possible for them to assure a permanent protection to the textiles and other substrate, such as paper, leather, etc., on which they are used. They may also be added to other polymers such as, in particular, natural or synthetic elastomers, butadiene-styrene and butadiene-acrylonitrile copolymers, chloropene polymer, acrylic elastomers, etc., to improve their surface properties.

The following examples illustrate the new products according to the invention.

The following examples 1 to 7 also employ a mixture of saturated and unsaturated perfluoroaliphatic amino compounds as reported in examples 8 to 13. However, the corresponding unsaturated amino compound was added to the reaction mixture together with the saturated amino compound and the individual quantities of the saturated and unsaturated compound obtained were reported as the total amount of perfluoroaliphatic amino compound reacted. Examples 14 and 15 did not yield a mixture of compounds.

EXAMPLE 1

Acrylic chloride (5 grams, 0.055 mole) was added drop by drop and under continuous agitation to a solution of $C_6F_{13}-C_2H_4-NH-CH_2CH_2OH$ (21 grams, 0.052 mole) and triethylamine (5 grams, 0.05 mole) in methylene chloride (60 cm$^3$), cooling the reaction vessel with an ice-water bath. After the reaction, the precipitated triethylamine chlorhydrate was filtered and ethyl ether was added to the filtrate to precipitate the triethylamine chlorhydrate remaining in solution in the methylene chloride. After filtration, the solvents were eliminated by prolonged evaporation under vaccuum. The viscous residual liquid (20 grams), which was difficult to purify, was made up of

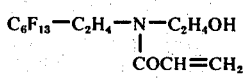

containing $C_6F_{13}C_2H_4NHC_2H_4$ $OCOCH=CH_2$ as an impurity.

EXAMPLE 2

Acrylic chloride (6.4 grams; 0.07 mole) was added drop by drop under continuous agitation to a solution of $C_6F_{13}C_2H_4$—NH—$CH_3$ (26 grams; 0.069 mole), triethylamine (7 grams; 0.07 mole), and hydroquinone (0.05 grams) in methyl chloride (65 cm³), cooling the reaction vessel with an ice bath. After the reaction, the precipitated triethylamine chlorhydrate was filtered, and ethyl ether was added to the filtrate to precipitate the triethylamine chlorhydrate remaining in solution in the methylene chloride. After filtration, the solvents were eliminated by evaporation under vacuum, hydroquinone was added (0.1 gram), and the residual liquid was distilled. There were thus obtained three fractions:
 a. light products/1 mm HG.: 1.2 grams. This fraction was made up essentially of methylene chloride;
 b. 86° C/1 mm Hg. fraction: 23.9 grams. This fraction was made up of

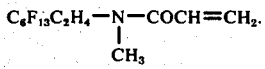

c. Residue: 1.3 grams of a polymerized solid
The yield of the experiment reached 80%.

EXAMPLE 3

Acrylic chloride (15 grams; 0.16 mole) was added drop by drop, under continuous agitation, to a solution of $C_6F_{13}$—$C_2H_4$—NH—$C_4H_9$ (63 grams; 0.15 mole), triethylamine (16 grams; 0.16 mole), and hydroquinone (0.1 grams) in methylene chloride (160 grams), cooling the reaction vessel with an ice bath. After reaction, the triethylamine chlorhydrate was filtered and ethyl ether was added to the filtrate to precipiate the triethylamine chlorhydrate remaining in solution in the methylene chloride. After filtration, the solvents were eliminated by evaporation under vacuum, hydroquinone was added (0.1 gram) and the residual liquid with a boiling point near 100° C under a pressure of 5×10⁻¹ mm Hg. (64.5 grams). This liquid was made up of an acrylamide with the formula

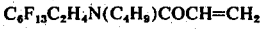

The yield of the experiment reached 90%.

EXAMPLE 4

A mixture of $C_6F_{13}$—$C_2H_4$—NH—$CH_3$ (18.85 grams; 0.05 mole), methyl acrylate (21.5 grams; 0.25 mole), and phenylenediamine (0.1 gram) was held at 90°–95° for 4 hours. As they arrived at the head of the distillation column, the light products passing between 62° and 80° were eliminated. After four hours the residual liquid was separated into fractions:
 a. 80° fraction, 16 grams, made up of methyl acrylate;
 b. 75°/1 mm fraction, 1.6 grams;
 c. 82°–85°/1 mm fraction, 18.1 grams, made up of $C_6F_{13}C_2H_4(CH_3)COCH=CH_2$.
The yield of the experiment is 84%.

EXAMPLE 5

In a flask, acrylyl chloride (4.33 grams; 0.048 mole) was added drop by drop under constant stirring to a solution of $C_8F_{17}$—$C_2H_4$—$NH_n$—$C_4H_9$ (24.7 grams; 0.047 mole) triethylamine (4.7 grams; 0.047 mole), and hydroquinone (0.1 gram) in methylene chloride, (50 grams). During the addition of acrylyl chloride, the flask was cooled in an ice-water bath. Towards the end of the addition, the triethylamine hydrochloride formed was filtered off and ethyl ether was added to the filtrate in order to precipitate the triethylamien hydrochloride which remained in solution. After a second filtration, the solvents were eliminated by evaporation under vacuum. Hydroquinone (0.1 gram) was then added to the viscous residual liquid, which was distilled in a molecular distillation equipment. Thus, $C_8F_{17}$—$C_2$-$H_4$—N(n $C_4H_9$)—CO—CH=$CH_2$ (20.9 grams; 0.0365 mole) was obtained. It distilled over at 105°–115°/0.1 mm.

Conversion rate of $C_8F_{17}$—$C_2H_4$—N(n $C_4H_9$)—CO—CH=$CH_2$ is 77%.

EXAMPLE 6

In a flask, acrylyl chloride (6.1 grams; 0.066 mole) was added drop by drop under constant stirring to a solution of $C_6F_{13}$—$C_2H_4$—$NH_2$ (24.1 grams; 0.066 mole), triethylamine (6.7 grams; 0.066 mole), and hydroquinone (0.1 gram) in methylene chloride (65 grams). During the addition of acrylyl chloride, the flask was cooled in an ice-water bath. Towards the end of the addition, the triethylamine hydrochloride formed was filtered off, and ethyl ether was added to the filtrate in order to precipitate the triethylamine hydrochloride which remained in solution. After a second filtration, the solvents were eliminated by evaporation under vacuum. Finally, hydroquinone (0.1 gram) was added to the residual liquid, which was distilled, and yielded $C_6F_{13}$—$C_2H_4$—NH—CO—CH=$CH_2$ (20.3 grams; 0.0485 mole) distilling at 100°–110°/0.5 mm Hg.

Conversion rate for $C_6F_{13}$—$C_2H_4$—N-H—CO—CH=$CH_2$ is 74%.

EXAMPLE 7

In a flask, acrylyl chloride (4.8 grams; 0.050 mole) was added drop by drop under constant stirring to a solution of $C_{10}F_{21}$—$C_2H_4$—NH—$CH_3$ (28.85 grams; 0.050 mole), triethylamine (5.05 grams; 0.05 mole), and hydroquinone (0.1 gram) in methylene chloride (50 grams). During the addition of acrylyl chloride the flask was cooled in an ice-water bath. Towards the end of the addition, the triethylamine hydrochloride formed was filtered off and ethyl ether was added to the filtrate in order to precipitate the triethylamine hydrochloride which remained in solution. After a second filtration, the solvents were eliminated under vacuum. Finally, hydroquinone (0.1 gram) was added to the residual solid, which was sublimed at 140°–160°/0.1 mm Hg. Thus

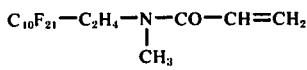

was obtained (26.2 grams; 0.0415 mole).

EXAMPLE 8

Acrylic chloride (6.4 grams) was added drop by drop under constant agitation to a solution of $C_5F_{11}=CH-CH_2-NH-CH_3$ (26 grams), $C_6F_{13}-C_2H_4-NH-CH_3$ (17.6 grams), triethylamine (7 grams) and hydroquinone (0.05 grams) in methylene chloride (65 cm³) with the reaction vessel cooled by an ice bath. After completion of the reaction, the triethylamine chlorhydrate remaining in the methylene chloride would precipitate. After filtration, the solvents were eliminated by evaporation under vacuum, hydroquinone (0.1 gram) was added, and the remaining liquid distilled. Three fractions were obtained:

a. Volatile Products/1 mm Hg.: weighing 1.2 gram contained mostly methylene chloride.
b. 86° C/1 mm Hg. fraction: weighing 23.9 grams contained 14%

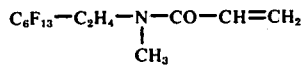

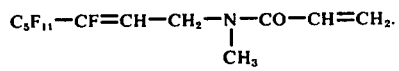

c. Residue: an unidentified polymerized solid weighing 1.3 gram.

Yields were 11% for

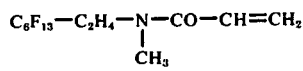

and 69% for

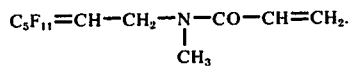

EXAMPLE 9

$C_5F_{11}-CF=CH-CH_2-NH-CH_3$ (18 grams), $C_6F_{13}-C_2H_4-NH-CH_3$ (1.9 gram), methylacrylate (21.5 grams) and p-phenylenediamine (0.1 gram) were held at 90°–95° C for 4 hours. As they arrived at the head of the distillation column, the volatile products passing between 62° and 80° were eliminated. After 4 hours, the residual liquid was separated into four fractions:

a. 80° C fraction, weighing 16 g. was methyl acrylate
b. 75° C/1 mm Hg. fraction: 1.6 gram.
c. 82°–85° C/1 mm Hg. fraction: 17.3 grams contained 13%

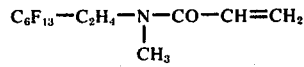

and 87%

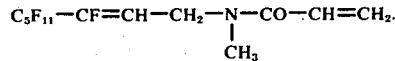

Yields were 11% for

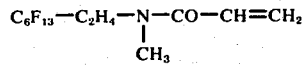

and 73% for

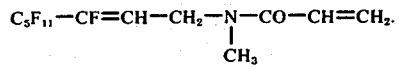

EXAMPLE 10

Acrylic chloride was added drop by drop into a flask containing a solution (28 grams) of 86% $C_9F_{19}CF=CH-CH_2-NH-CH_3$, and 14% $C_{10}F_{21}-C_2H_4-NH-CH_3$, triethylamine (5.05 grams) and hydroquinone (0.13 gram) in methylene chloride (50 grams). During the addition of the acrylyl chloride, the flask was cooled by an ice bath. At the end of the addition, the triethylamine chlorhydrate formed was filtered and ethyl ether was added to the filtrate in order to precipitate any triethylamine chlorhydrate remaining in solution. After a second filtration, the solvents were eliminated under vacuum. Hydroquinone (0.1 gram) was added to the solid residue which had sublimed at 140°–160° C at 0.1 mm Hg. There was thus obtained 25.5 grams of a mixture of 89%.

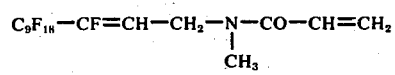

and 11%

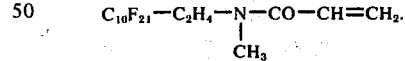

EXAMPLE 11

Acrylyl chloride (7.2 grams) was added drop by drop under constant stirring to a reaction flask containing a mixture (30.8 grams) of $C_5F_{11}CF=CH-CH_2-NH-C_4H_9$ and $C_6F_{13}-C_2H_4-NH-C_4H_9$ and triethylamine (7.5 grams) in methylene chloride (65 cm³). During the addition of the acrylyl chloride, the reaction flask was cooled with an ice bath. As soon as the acrylic chloride was introduced, a white solid consisting of triethylamine chlorhydrate appeared. The solid was filtered and ethyl ether added to the filtrate to eliminate any triethylamine chlorhydrate remaining in the methylene chloride. After filtration, the solvents were evaporated and molecular distillation of the remaining viscous liquid was carried out at 5×10⁻²mm Hg. A mixture of 13.4 grams C₆F₁₃—C₂H₄—N—(C₄H₉)—CO—CH=CH₂ (Yield = 37.5%) and 14.5 grams C₅F₁₁CF=CH₂—N—(C₄H₉)—CO—CH=CH₂ (Yield — 42.5%) was obtained.

EXAMPLE 12

Acrylyl chloride (4.33 grams) was added drop by drop under constant stirring to a reaction flask containing a mixture (24.2 grams of 0.047 mole C₇F₁₅—CF=λCH—CH₂—NH—nC₄H₉ and 0.025 mole C₈F₁₇—C₂H₄—NH—nC₄H₉, triethylamine (4.7 grams) and hydroquinone (0.1 gram) in methylene chloride (50 grams). During the addition of the acrylyl chloride, the flask was cooled with an ice bath. At the end of the addition, the triethylamine formed was filtered and ethyl ether was added to the filtrate to precipitate any triethylamine chlorhydrate remaining in the solution. After a second filtration, the solvents were eliminated by evaporation under vacuum. Hydroquinone (0.6 grams) was added to the remaining viscous liquid which was then distilled by means of molecular distillation apparatus. 20.5 grams of a mixture coming off at 105°–115°/0.1 mm Hg. containing

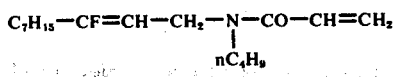

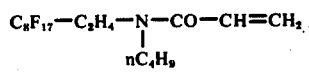

were obtained.

EXAMPLE 13

Acrylic chloride (11.7 grams) were added drop by drop with constant agitation to a solution (49 grams) containing 0.042 mole

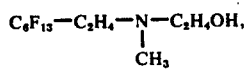

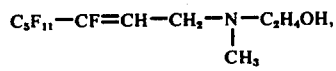

and hydroquinone (0.19 grams) in methylene chloride (120 grams) while maintaining a temperature below 5° C by means of an ice bath. After the reaction, the triethylamine precipitate was filtered and ethyl ether was added to the filtrate in order to precipitate any triethylamine chlorhydrate remaining in the methylene chloride. After filtration, the solvents were removed by vacuum evaporation. Hydroquinone (0.1 gram) was added to the resinal liquid which was distilled yielding two fractions.

a. 90°–100°/0.05 mm Hg. fraction: weighing 46 grams contained 34%

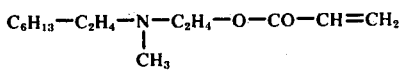

(Yield = 28.8%) and 66%

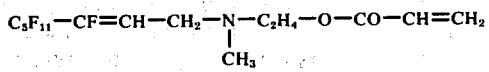

Yield = 56.28%).

EXAMPLE 14

In a flask, acrylyl chloride (4.8 grams; 0.050 mole) was added drop by drop under constant stirring to a solution of C₆F₁₃(C₂H₄)₂NH—CH₃ (20.0 grams; 0.050 mole), triethylamine (5.06 grams; 0.050 mole), and hydroquinone (0.1 gram) in methylene chloride, the flask was cooled in an ice-water bath. Towards the end of the addition, the triethylamine hydrochloride formed was filtered off, and ethyl ether added to the filtrate in order to precipitate the triethylamine hydrochloride which remained in solution. After a second filtration, the solvents were eliminated by evaporation under vacuum. Finally, hydroquinone (0.1 gram) was added to the residual liquid, which was distilled in a molecular distillation apparatus. Thus

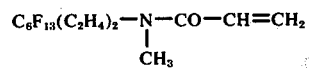

(17.4 grams; 0.038 mole) boiling at 100°–110°/0.1 Hg. was obtained.

Conversion rate for

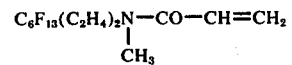

is 76%.

EXAMPLE 15

In a flask, acrylyl chloride (3.5 grams; 0.036 mole) was added drop by drop under constant stirring to a solution of C₈F₁₇(C₂H₄)₂NH₂ (17.6 grams; 0.036 mole), triethylamine (3.65 grams; 0.036 mole), and hydroquinone (0.1 gram) in methylene chloride (25 grams). During the addition of the acrylyl chloride, the flask was cooled in an ice-water bath. Towards the end of the addition, the triethylamine hydrochloride formed was filtered off, and ethyl ether added to the filtrate in order to precipitate the triethylamine hydrochloride which remained in solution. After a second filtration, the solvents were eliminated by evaporation under vacuum. Hydroquinone (0.1 gram) was added to the residual solid, which was sublimed between 140° and 160° under 0.1 mm Hg. Thus, C₈F₁₇(C₂H₄)₂NH—CO—CH=CH₂ (15.1 grams; 0.028 mole) was obtained.

Conversion rate for C₈H₁₇(C₂H₄)₂NH—CO—CH=CH₂ is 77%.

We claim:
1. A perfluoralkyl substituted amino compound of the formula

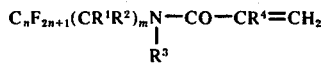

wherein n is an integer from 6 to 20, m is 2 or 4, $R^1$ and $R^2$ each is hydrogen atom or a lower alkyl with 1 to 3 carbon atoms, $R^3$ is a hydrogen atom, an alkyl containing 1 to 20 carbon atoms, an alkenyl containing 3 to 10 carbon atoms, a cycloalkyl radical containing 3 to 12 carbon atoms, a cycloalkenyl with 5 to 12 carbon atoms, an N or O ring substituted cycloalkenyl radical containing 5 to 12 carbon atoms, an aryl, the radical of —$(CHR)_q$—OH wherein R is a hydrogen atom or a lower alkyl containing 1 to 3 carbon atoms, and $R^4$ is a hydrogen atom or a methyl group.

2. A compound according to claim 1 wherein n is from 6 to 12, m is 2 and at least one of the radicals $R^1$ and $R^2$ is hydrogen.

3. An amine according to claim 2 wherein the amine has the formula

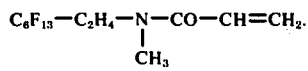

4. An amine according to claim 2 wherein the amine has the formula

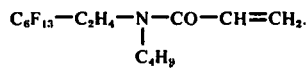

5. A compound according to claim 1 wherein n is from 6 to 12 and m is 4.

6. A compound according to claim 5 wherein the compound has the formula

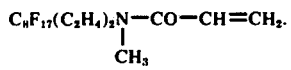

7. A composition of matter comprising a perfluoralkyl substituted amino compound of the formula

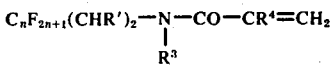

together with a perfluoraliphatic substituted amino compound of the formula

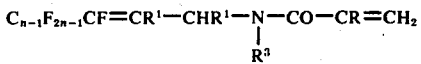

wherein $R^1$, $R^3$ and $R^4$ have the same meaning as defined in claim 1 and n is an integer from 4 to 20.

8. A composition of matter according to claim 7 comprising the compound

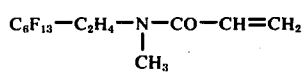

together with the compound

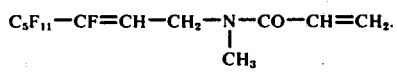

9. A composition of matter according to claim 7 comprising the compound

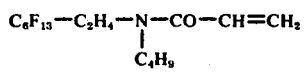

together with the compound

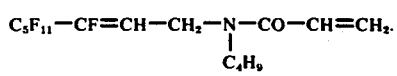

* * * * *

UNITED STATES PATENT AND TRADEMARK OFFICE
CERTIFICATE OF CORRECTION

PATENT NO. : 3,997,604
DATED : December 14, 1976
INVENTOR(S) : Louis Foulletier and Jean-Pierre Lalu It is certified that error appears in the above-identified patent and that said Letters Patent are hereby corrected as shown below:

Column 3, Line 51    "20°", should read --0°--

Column 4, Line 11    "V is a atom, atome," should read --V is a chlorine atom--

Column 9, Lines 10 and 11    "CF=λCH", should read --CF=CH--

Column 9, Line 27    "$H_{15}$", should read --$F_{15}$--

Column 9, Line 46    "OH" should read --OH, 0.078 mole--

Column 9, Line 56    "OH and hydroquinone" should read --OH, triethylamine (12 grams) and hydroquinone--

Column 10, Line 1    "$H_{13}$" should read --$F_{13}$--

Signed and Sealed this

Twelfth Day of April 1977

[SEAL]

Attest:

RUTH C. MASON
Attesting Officer

C. MARSHALL DANN
Commissioner of Patents and Trademarks